United States Patent [19]

Ludmirsky et al.

[11] Patent Number: 4,967,186
[45] Date of Patent: Oct. 30, 1990

[54] METHOD AND APPARATUS FOR FATIGUE DETECTION

[76] Inventors: Ariold Ludmirsky, 46 Hatayasim, Jerusalem 92509; Arie Zigler, 23 Ostashinsky, Rishon Le Zion, both of Israel

[21] Appl. No.: 395,466

[22] Filed: Aug. 18, 1989

[51] Int. Cl.⁵ .................. G08B 23/00; A61B 3/14
[52] U.S. Cl. ...................... 340/575; 351/210
[58] Field of Search .............. 340/575, 576, 556; 351/210, 221; 250/221

[56] References Cited

U.S. PATENT DOCUMENTS

| | | | |
|---|---|---|---|
| 2,724,109 | 11/1955 | Skolnick et al. | 340/575 |
| 3,524,030 | 8/1970 | Wiegel | 340/575 |
| 3,863,243 | 1/1975 | Skolnick et al. | 340/575 |
| 4,144,531 | 3/1979 | Anbergen | 340/575 |
| 4,145,122 | 3/1979 | Rinard et al. | 351/7 |
| 4,257,688 | 3/1981 | Matsumura | 351/7 |
| 4,397,531 | 8/1983 | Lees | 351/210 |
| 4,623,230 | 11/1986 | Weinblatt | 351/210 |
| 4,659,197 | 4/1987 | Weinblatt | 351/210 |
| 4,725,824 | 2/1988 | Yoshioka | 340/575 |
| 4,815,839 | 3/1989 | Waldorf | 351/210 |

FOREIGN PATENT DOCUMENTS 0284255 9/1989 European Pat. Off.

*Primary Examiner*—Joseph A. Orsino
*Assistant Examiner*—Thomas J. Mullen, Jr.
*Attorney, Agent, or Firm*—Lowe, Price, LeBlanc, Becker & Shur

[57] ABSTRACT

A method and apparatus is disclosed which is capable of detecting an individual's level of fatigue and generating an alarm signal in accordance therewith. The level of fatigue is determined based on changes in the reflectivity of a projected IR beam which is reflected off an eyelid. At initial stages of drowsiness the eyelid is relatively rough and the reflectivity is lower than when the eyelid fully closes as when a person is heavily fatigued.

10 Claims, 2 Drawing Sheets

METHOD AND APPARATUS FOR FATIGUE DETECTION

BACKGROUND OF THE INVENTION

The present invention is directed to a method and apparatus for detecting the fatigue or drowsiness level of an individual. In particular, the present invention is directed to a method and apparatus which detects the difference in infra-red (IR) light reflection from the eye fundus and eyelid to determine the level of fatique and trigger an alarm.

There is a recognized need for a safety device which is capable of warning and arousing an operator who has become drowsy while operating various machines or vehicles. For example, U.S. Pat. No. 4,144,531 issued to Aubergen discloses a safety apparatus that directs a wave along a path close to an individual's eyeball. The wave is interrupted by the eyelashes when the person blinks or closes his eye and a warning signal is generated in response to the interruption of the wave. One drawback to such conventional devices is that they are not capable of detecting the degree of fatique or drowsiness of an individual thereby causing many false alarms.

An object of the present invention is to provide a method and apparatus that is capable of detecting an individual's level of fatigue. A further object of the invention is to generate alarm signals based on an individual's fatigue level.

SUMMARY OF THE INVENTION

The present invention accomplishes the above objects by utilizing a light emitter and detector, which preferrably operate at IR wavelengths, to detect whether a person has closed his eye. The reflectivity of the eyelid is a function of the skin roughness. At initial stages of drowsiness the eyelid is relatively rough and the reflectivity into the detector is lower than that occurring under conditions of fatigue when the eye lid totally closes. The light reflected from the eyelid is translated into electrical signals which are amplified. As the eyelid closes, the reflectivity changes resulting in a change in the electrical signal. Alarm signals can then be generated when the electrical signal reaches certain thresholds, or a general warning alarm can be increased from a low level at an initial stage of fatigue to a high level when the eye lid is completely closed.

BRIEF DESCRIPTION OF THE DRAWINGS

With the above as background, reference should now be made to the following detailed description of the preferred embodiments and the accompanying drawings in which.

DETAILED DESCRIPTION OF PREFERRED EMBODIMENTS

Figure 1:
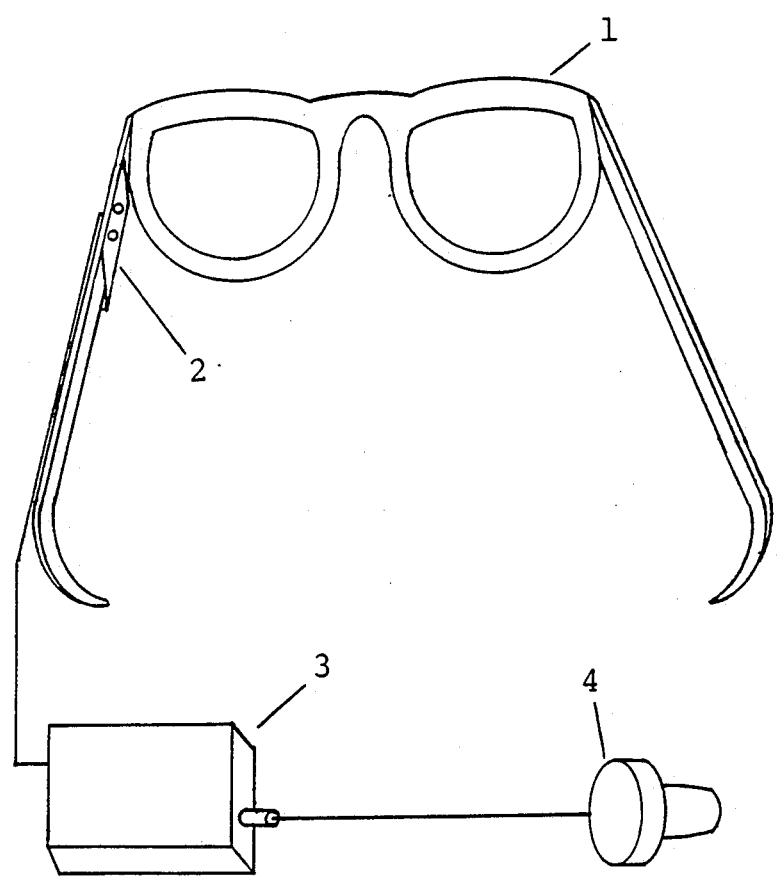
FIG. 1 illustrates a preferred embodiment of the invention.

Referring now to FIG. 1, a fatigue detection apparatus is shown including an eyeglass frame 1, a emitter-receiver light collection assembly 2, electronic circuitry assembly 3, and earpiece 4. While the electronic circuitry assembly 3 and earpiece 4 are shown as elements separate from the eyeglass frame, it will be readily appreciated by one of ordinary skill in the art that such elements could be incorporated into the eyeglass frame itself using miniaturized components. Alternatively, the earpiece 4 can be replaced entirely by a small speaker located within the external electronic circuitry assembly 3 if it is external as shown in FIG. 1, or located within the eyeglass frame.

Figure 2:
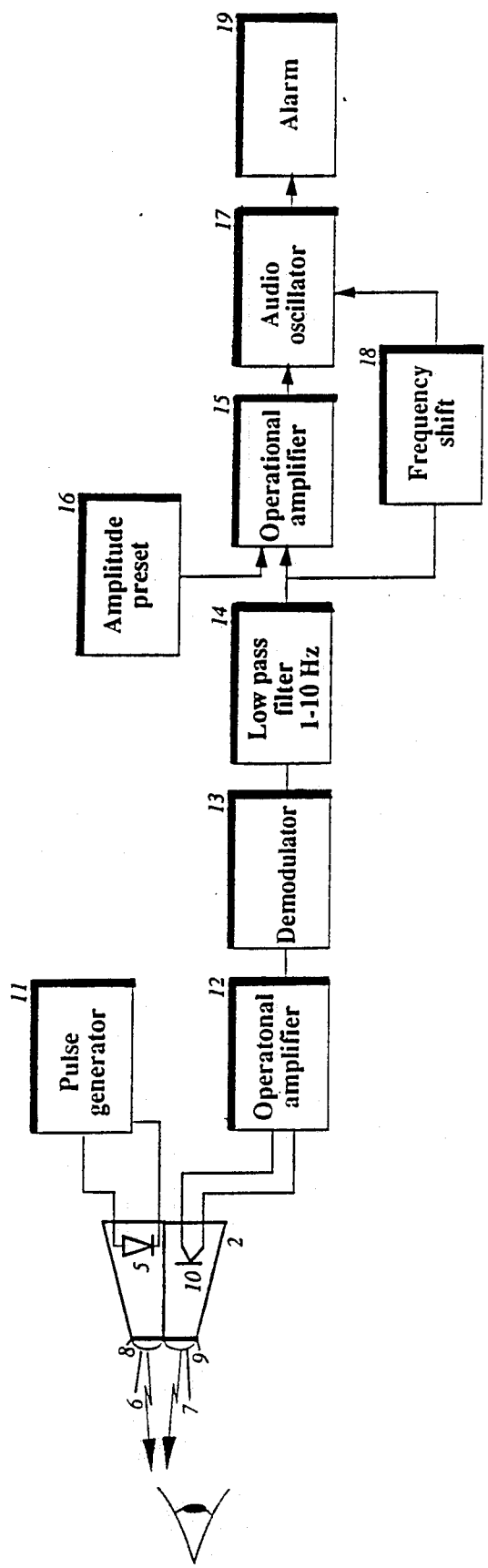
FIG. 2 is a schematic block diagram of the electrical circuits employed in the preferred embodiment illustrated in FIG. 2.

As shown in FIG. 2, the emitter-receiver light collection assembly 2 includes an IR light emitting diode 5, focusing lenses 6 and 7, and narrow band IR filters 8 and 9. Light emitted from the diode 5 passes through the IR filter 8 and is focused on a point of the eye funds via the focusing lens 6. Reflected diffuse light is collected by lens 7 and focused onto a solid state photo-transistor 10.

Preferably, the emitting diode 5 radiates light at 800 nm, modulated by the electrical power received from a high frequency (10 KHz) pulse generator 11 which operates at a low duty cycle (1:100). This provides a substantial reduction in the amount of light impinging the eye in contrast to constant illumination. Electrical signals produced by the photo-transistor 10 are amplified by an operational amplifier 12 and demodulated by a demodulator 13.

The demodulated signal is supplied to a low frequency pass filter 14, adjustable in a range of 1 to 10 Hz, which discriminated between natural eye blinking and eye shutting for significant period of time (for example above 300 milliseconds) which are indicative of fatigue. Pulses lasting for longer that the prescribed time period are passed to a threshold amplifier 15 which amplifies only those signals with an amplitude above a preset level set by an amplitude preset circuit 16. The preset level is based on the substantially high reflectivity of the eyelid in comparison to the reflectivity of the eye fundus.

The duration of the signal obtained from the threshold amplifier 15, therefore, is equal to the period over which the eyelid is closed, and the amplitude of the signal is proportional to the amount of light reflected by the eyelid. As previously stated, the reflectivity of the eyelid is proportional to the roughness of the eyelid. It has been found that the eyelid will not close as tightly as when a person is lightly fatigued as when heavily fatigued, which results in differences in the roughness of the eyelid and consequently the reflectivity of the eyelid. Thus, the amplitude of the obtained signal is directly indicative of the level of fatigue.

The signal obtained from the threshold amplifier 15 is supplied to an audio amplifier 17 which operates only in response thereto. The demodulated signal is supplied to the frequency shifter 18, which changes the frequency of the audio amplifier 17 in accordance with the amplitude of the demodulated signal. The output signal from the audio amplifier 17 is then supplied to the earpiece 4. The alarm sound heard in the earpiece, therefore, occurs only when the eye has been closed for a certain period of time, and the frequency of the sound varies directly in proportional to the fatigue of the individual. Accordingly, a low level alarm signal is produced when a person is lightly fatigued and a higher level alarm signal is produce when a person is heavily fatigued.

The invention has been described with reference to certain preferred embodiments thereof, but it will be understood that modifications and variations are possible within the scope of the appended claims. For example, alarm signals could be generated based on the comparison of the amplitude of the low pass components of the demodulated signal to predetermined thresholds instead of generating variable alarm signal. Also, the invention is not limited to the specific type of detection circuitry described with respect to the preferred embodiment, but encompasses any circuitry which performs the functions outlined above. In addition, the invention is not limited to the use of an eyeglass frame, as any structure suitable for properly locating the emitter-receiver light collection assembly may be used.

What is claimed is:

1. An apparatus for detecting fatigue, said apparatus comprising:
    source means for generating and reflecting an IR light beam off a point of a persons eye;
    detector means for receiving the reflected IR light beam and generating a sensed signal in response thereto; and
    processing means for comparing the amplitude and duration of said sensed signal generated by said detector means to predetermined amplitude and duration threshold values and generating an alarm signal when said predetermined threshold values are exceeded by said signal, wherein said processing means includes means for varying said alarm signal in accordance with variations in said sensed signal that are indicative of a fatigue level.

2. An apparatus as claimed in claim 1, wherein said source means modulates said IR light beam.

3. An apparatus as claimed in claim 1, further comprising an alarm unit that generates an audible driver alert signal in response to said alarm signal.

4. An apparatus for detecting fatigue, said apparatus comprising:
    source means for generating and reflecting an IR light beam off a point of a persons eye, wherein said IR light beam is modulated by said source means at a frequency of approximately 10 KHz;
    detector means for receiving the reflected IR light beam and generating a signal in response thereto; and
    processing means for comparing the amplitude and duration of said signal generated by said detector means to predetermined amplitude and duration threshold values and generating an alarm signal when said predetermined threshold values are exceeded by said signal.

5. An apparatus as claimed in claim 4, further comprising an alarm unit that generates an audible driver alert signal in response to said alarm signal.

6. An apparatus for detecting fatigue, said apparatus comprising:
    source means for generating and reflecting an IR light beam off a point of a persons eye;
    detector means for receiving the reflected IR light beam and generating a signal in response thereto; and
    processing means for comparing the amplitude and duration of said signal generated by said detector means to predetermined amplitude and duration threshold values and generating an alarm signal when said predetermined threshold values are exceeded by said signal;
    wherein said predetermined threshold for the duration of said signal is about 300 milliseconds.

7. An apparatus as claimed in claim 6, further comprising an alarm unit that generates an audible driver alert signal in response to said alarm signal.

8. A method for detecting fatigue comprising the steps of:
    generating and reflecting an IR light beam off a point of a persons eye;
    receiving the reflected IR light beam and generating a sensed signal in response thereto;
    comparing the amplitude and duration of said sensed signal to predetermined amplitude and duration threshold values and generating an alarm signal when said predetermined threshold values are exceeded by said signal; and
    varying said alarm signal in response to variations in said sensed signal that are indicative of a fatigue level.

9. A method as set forth in claim 8, further comprising the step of generating an audible driver alert signal in response to said alarm signal.

10. An apparatus comprising: an infrared light source coupled to a pulse generator; a lens system adapted to focus IR light generated by said light source on a selected point of an individual's eye; a photodetector arranged to receive IR light reflected from the individual's eye and generate a modulated signal; a demodulator configured to receive said modulated signal and generate a demodulated signal; a low pass filter coupled to said demodulator to receive said demodulated signal and pass low frequency components of said demodulated signal; a threshold amplifier coupled to said low pass filter to receive said low frequency components and generate a trigger signal when said low frequency components exceed a set threshold level; and an oscillator coupled to a frequency shift unit that receives said low frequency components, wherein said oscillator is responsive to said trigger signal and to said frequency shift unit to generate an alarm signal having a frequency related to the amplitude of said demodulated signal.

* * * * *